(12) United States Patent
Hosokai et al.

(10) Patent No.: US 12,070,191 B2
(45) Date of Patent: Aug. 27, 2024

(54) HOLDING FRAME, ENDOSCOPE DISTAL END STRUCTURE, AND ENDOSCOPE

(71) Applicant: OLYMPUS CORPORATION, Tokyo (JP)

(72) Inventors: Shigeru Hosokai, Hachioji (JP); Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 529 days.

(21) Appl. No.: 17/380,291

(22) Filed: Jul. 20, 2021

(65) Prior Publication Data

US 2021/0345861 A1 Nov. 11, 2021

Related U.S. Application Data

(63) Continuation of application No. PCT/JP2019/011291, filed on Mar. 18, 2019.

(51) Int. Cl.
*A61B 1/05* (2006.01)
*A61B 1/00* (2006.01)

(52) U.S. Cl.
CPC .......... *A61B 1/051* (2013.01); *A61B 1/00018* (2013.01); *A61B 1/00147* (2013.01); *A61B 1/00009* (2013.01)

(58) Field of Classification Search
CPC .................................................. A61B 1/00018
See application file for complete search history.

(56) References Cited

U.S. PATENT DOCUMENTS

| 8,870,753 B2 * | 10/2014 | Boulais .............. A61B 1/00105 600/156 |
|---|---|---|
| 2015/0085169 A1 | 3/2015 | Igarashi et al. |
| 2016/0126286 A1 | 5/2016 | Igarashi et al. |

(Continued)

FOREIGN PATENT DOCUMENTS

| CN | 202748535 U | 2/2013 |
|---|---|---|
| CN | 104380465 A | 2/2015 |

(Continued)

OTHER PUBLICATIONS

International Search Report dated Jun. 11, 2019 issued in PCT/JP2019/011291.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

A holding frame for an imaging unit arranged at a distal end of an endoscope includes a cylindrical three-dimensional molded interconnect device; a housing configured to house the imaging unit, the housing being formed of a notch; at least one cut face formed on the side face of the holding frame and obtained by cutting a support portion which is a gate portion into which a resin is injected when the holding frame is resin-molded; a connection terminal formed on a bottom face of the housing portion and configured to be connected to the imaging unit; a cable connection electrode arranged on a face where a proximal end side of the holding frame is notched; and a wiring pattern formed on a surface area of the holding frame excluding the cut face and configured to electrically connect the connection terminal and the cable connection electrode.

17 Claims, 10 Drawing Sheets

(56) References Cited

U.S. PATENT DOCUMENTS

| | | | |
|---|---|---|---|
| 2017/0127915 A1* | 5/2017 | Viebach | ............... A61B 1/018 |
| 2017/0251906 A1 | 9/2017 | Hatano | |
| 2021/0307590 A1* | 10/2021 | Wakito | ................ G02B 23/26 |
| 2021/0382293 A1* | 12/2021 | Kodama | ............ G02B 23/2484 |
| 2021/0401267 A1* | 12/2021 | Kodama | ............ A61B 1/00097 |

FOREIGN PATENT DOCUMENTS

| | | |
|---|---|---|
| CN | 106061350 A | 10/2016 |
| CN | 107072502 A | 8/2017 |
| JP | H11-305146 A | 11/1999 |
| JP | 2017-505154 A | 2/2017 |

* cited by examiner

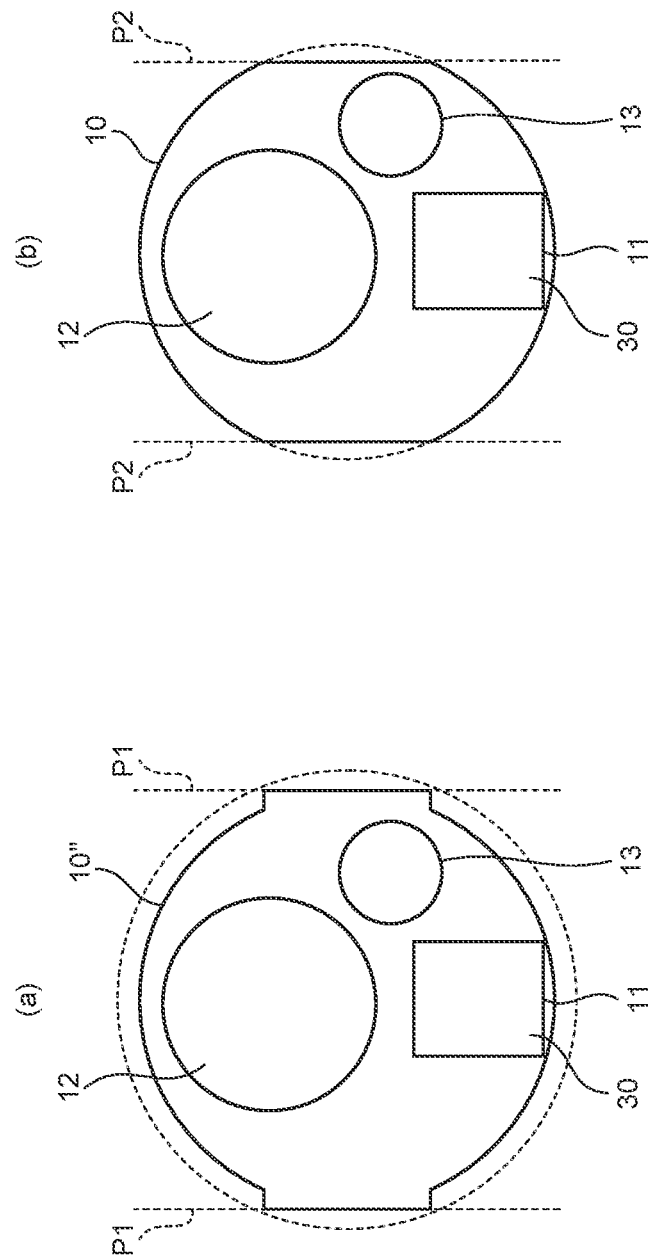

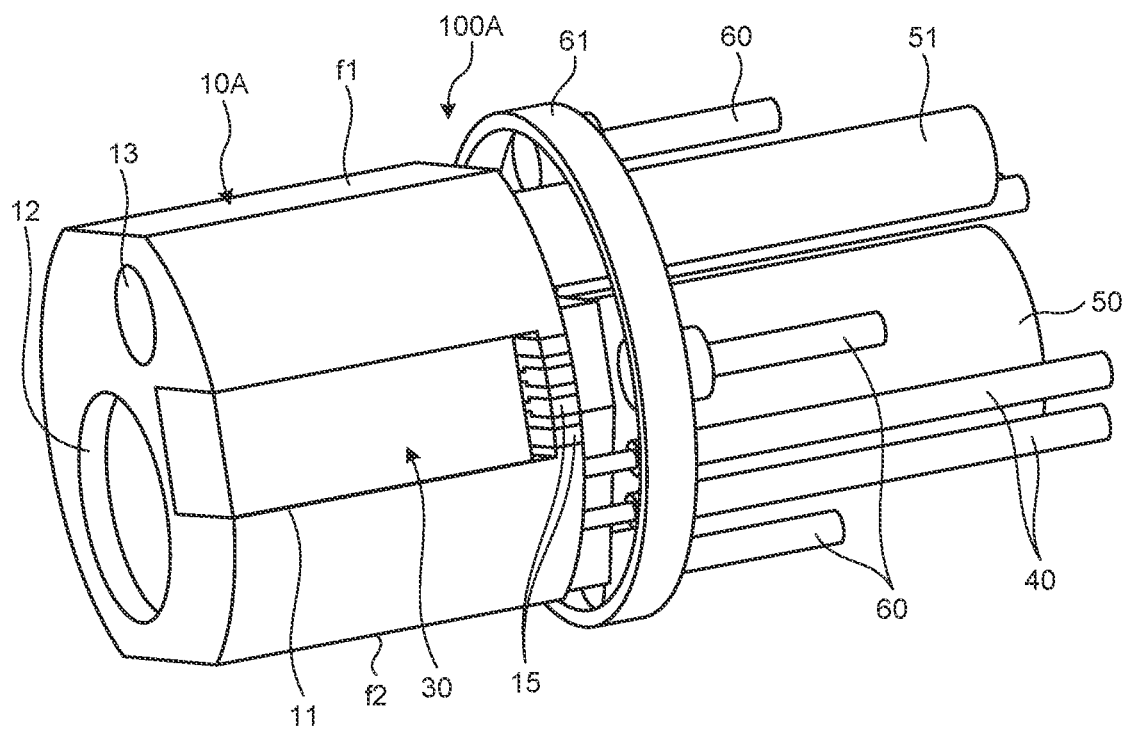

HOLDING FRAME, ENDOSCOPE DISTAL END STRUCTURE, AND ENDOSCOPE

This application is a continuation of International Application No. PCT/JP2019/011291, filed on Mar. 18, 2019, the entire contents of which are incorporated herein by reference.

BACKGROUND

The present disclosure relates to a holding frame, an endoscope distal end structure, and an endoscope.

In the related art, an endoscope acquires image data in a subject by means of an imaging unit arranged at a distal end portion thereof by inserting a flexible insertion unit having an elongated shape provided with an imaging unit at the distal end into the subject, and transmits the image data to an external information processing device by means of a signal cable. Although the imaging unit is held in a holding frame in order to fix its position relative to other internal components, an endoscope in which the holding frame is switched from a metal to a resin has been proposed recently.

SUMMARY

According to one aspect of the present disclosure, there is provided a holding frame for an imaging unit arranged at a distal end of an endoscope, the holding frame including: a cylindrical three-dimensional molded interconnect device; a housing configured to house the imaging unit, the housing being formed of a notch at a corner of a distal end face of the holding frame and a side face of a distal end side of the holding frame; at least one cut face formed on the side face of the holding frame and obtained by cutting a support portion which is a gate portion into which a resin is injected when the holding frame is resin-molded; a connection terminal formed on a bottom face of the housing portion and configured to be connected to the imaging unit; a cable connection electrode arranged on a face where a proximal end side of the holding frame is notched; and a wiring pattern formed on a surface area of the holding frame excluding the cut face and configured to electrically connect the connection terminal and the cable connection electrode.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is a view for explaining a cut face of the holding frame of FIG. 2;

FIG. 12 is a perspective view of the endoscope distal end structure of FIG. 11 from another direction.

DETAILED DESCRIPTION

Figure 1:
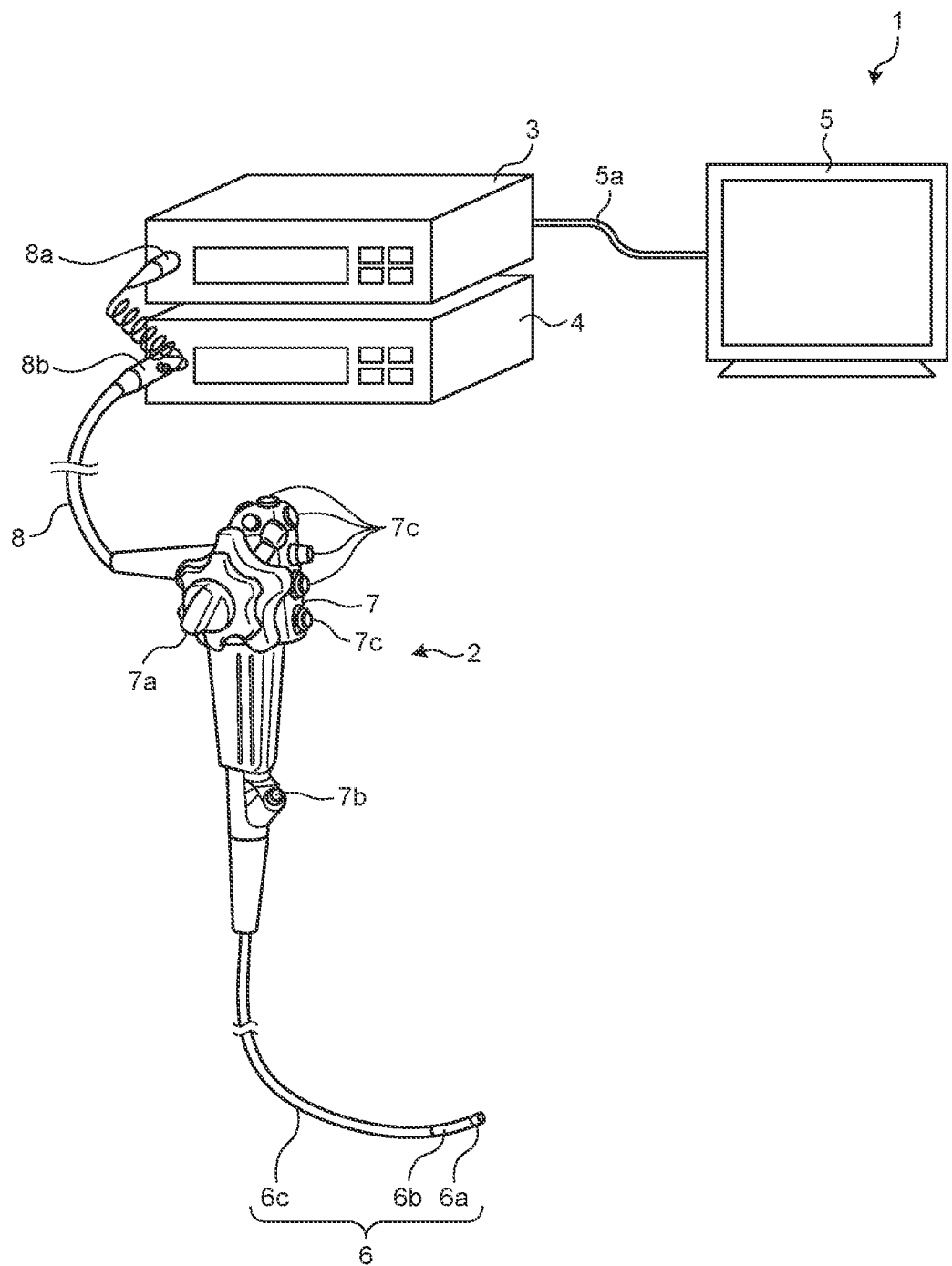
FIG. 1 is a view schematically illustrating an overall configuration of an endoscope system according to a first embodiment.

In the following description, an endoscope system including an endoscope distal end structure will be described as a mode for carrying out the present disclosure (hereinafter referred to as "embodiment"). The present disclosure is not limited by this embodiment. Further, in the drawings, the same portions are denoted by the same reference numerals. Further, it is necessary to note that the drawings are schematic illustration in which the relationships between the thickness and the width of each member, and the proportions of each member, for example, may differ from the actual relationships and proportions. In addition, there may be differences in dimensions and proportions between the drawings.

FIG. 1 is a view schematically illustrating an overall configuration of an endoscope system 1 according to a first embodiment. As illustrated in FIG. 1, the endoscope system 1 according to the first embodiment includes: an endoscope 2 which is introduced into a subject and captures the inside of the subject to generate an image signal of the inside of the subject; an information processing device 3 which performs predetermined image processing on the image signal obtained by the capturing by the endoscope 2 and controls each part of the endoscope system 1; a light source device 4 which generates illumination light of the endoscope 2; and a display device 5 which displays the image signal after image processing by the information processing device 3.

The endoscope 2 includes an insertion unit 6 inserted into the subject, an operating unit 7 held by an operator on the proximal end portion side of the insertion unit 6, and a flexible universal cord 8 extending from the operating unit 7.

The insertion unit 6 is implemented by using a light guide cable, an electric cable, and an optical fiber, for example. The insertion unit 6 has a distal end portion 6a which incorporates an imaging unit to be described below, a bendable bending portion 6b including a plurality of bending pieces, and a flexible tube portion 6c provided on the proximal end portion side of the bending portion 6b. The distal end portion 6a is provided with a light guide cable for illuminating the inside of the subject, an imaging unit for capturing the inside of the subject, and an opening for communicating a channel for a treatment tool.

The operating unit 7 has: a bending knob 7a for bending the bending portion 6b in the vertical and horizontal directions; a treatment tool insertion portion 7b in which treatment tools such as biological forceps and a laser scalpel are inserted into the body cavity of the subject; and a plurality of switch portions 7c for operating peripheral devices such as the information processing device 3, the light source device 4, an air supply device, a water supply device, and a gas supply device. The treatment tool inserted from the treatment tool insertion portion 7b comes out from the opening of the distal end of the insertion unit 6 through a treatment tool channel provided inside of the insertion unit.

The universal cord 8 is formed by using a light guide cable, and an electric cable, for example. The universal cord 8 is branched at its proximal end. One of the branched ends is a connector 8a and the other proximal end is a connector 8b. The connector 8a is attachable to and detachable from a connector of the information processing device 3. The connector 8b is attachable to and detachable from the light source device 4. The universal cord 8 propagates the illumination light emitted from the light source device 4 to the distal end portion 6a via the connector 8b and the light guide cable. Further, the universal code 8 transmits the image signal obtained by capturing by the imaging unit to be described below to the information processing device 3 via the cable and the connector 8a.

The information processing device 3 performs predetermined image processing on the image signal outputted from the connector 8a and controls the entire endoscope system 1.

The light source device 4 is formed by using a light source for emitting light, and a condenser lens, for example. Under the control of the information processing device 3, the light source device 4 emits light from the light source and supplies the light to the endoscope 2 connected via the light guide cable of the connector 8b and the universal cord 8 as illumination light for the inside of the subject which is a subject to be imaged.

The display device 5 is formed by using, for example, a display using a liquid crystal or an organic EL (Electro Luminescence). The display device 5 displays various types of information including the images having been subjected to the predetermined image processing by the information processing device 3 via a video cable 5a. Thus, the surgeon may observe and determine properties of a desired position of the inside of the subject by operating the endoscope 2 while viewing the image (in-vivo image) displayed on the display device 5.

Figure 2:
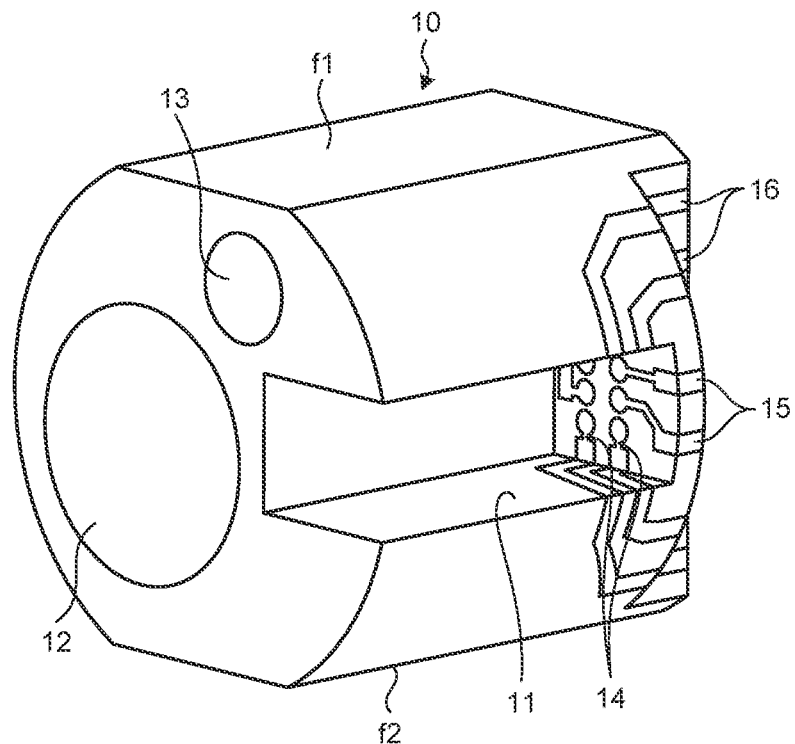
FIG. 2 is a perspective view from a distal end side of a holding frame of an imaging unit arranged at a distal end portion of the endoscope illustrated in FIG. 1.
Figure 3:
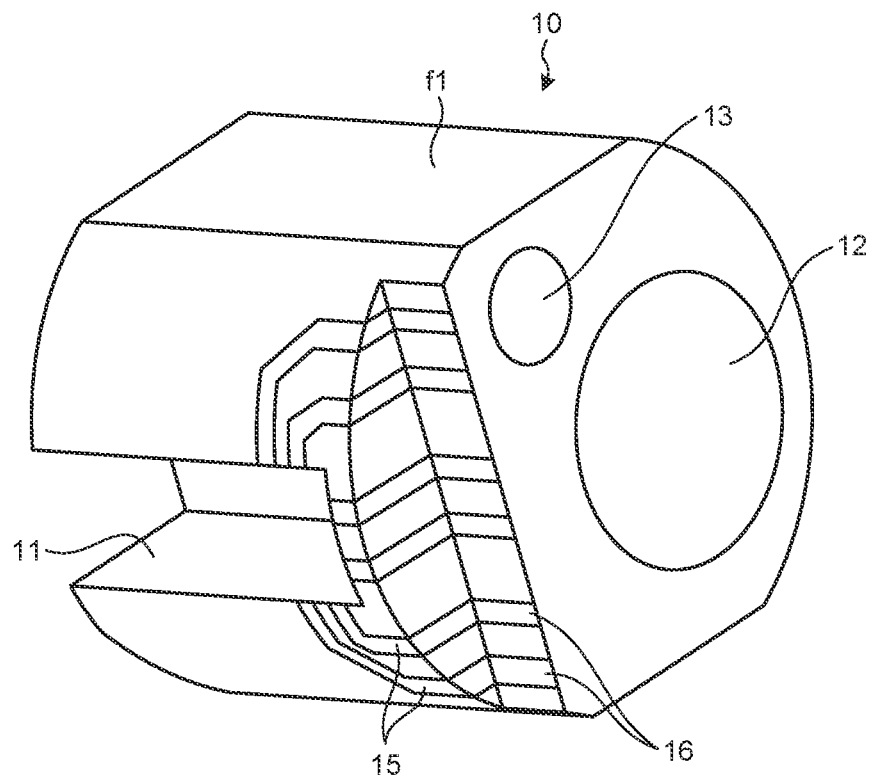
FIG. 3 is a perspective view from a proximal end side of the holding frame of FIG. 2.
Figure 4:
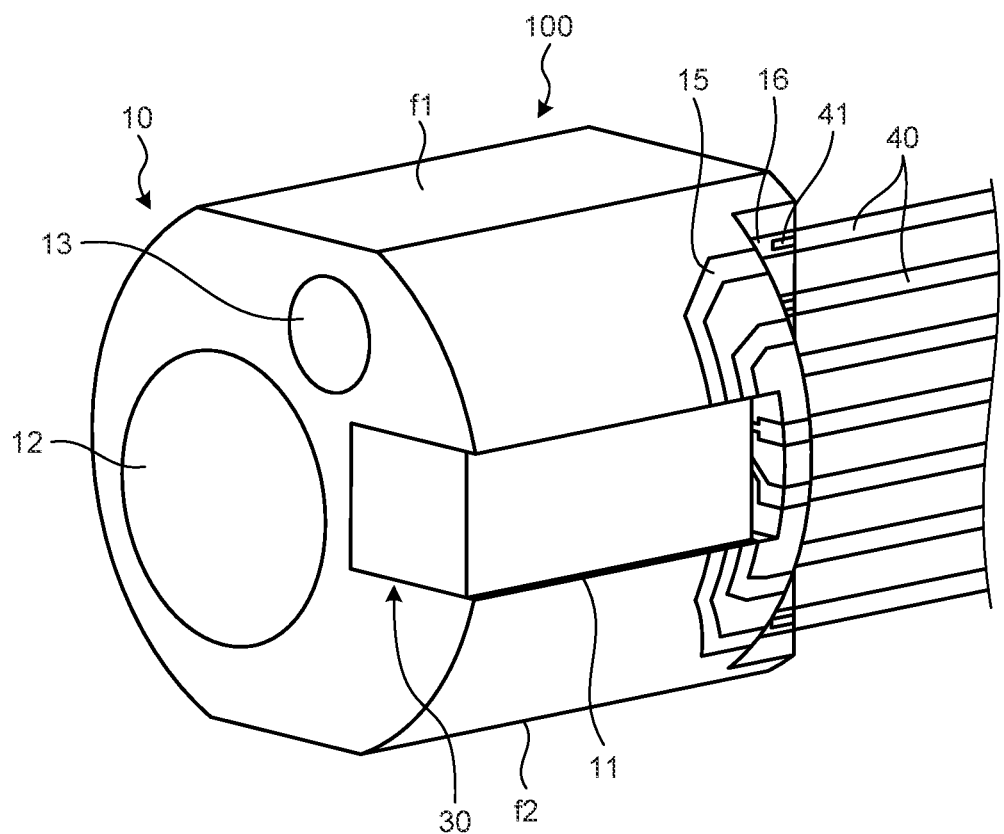
FIG. 4 is a perspective view of an endoscope distal end structure in which the imaging unit is housed in the holding frame of FIG. 2.

A holding frame and an endoscope distal end structure used in the endoscope system 1 will then be described in detail. FIG. 2 is a perspective view from the distal end side of a holding frame 10 of an imaging unit 30 arranged at the distal end portion of the endoscope 2 illustrated in FIG. 1. FIG. 3 is a perspective view from the proximal end side of the holding frame 10 of FIG. 2. FIG. 4 is a perspective view of an endoscope distal end structure 100 in which the imaging unit 30 is housed in the holding frame 10 of FIG. 2. FIG. 4 omits the illustration of the light guide and the channel. In the present description, the distal end portion 6a side of the endoscope 2 is referred to as a distal end side, and the side on which a signal cable 40 extends is referred to as a proximal end side. Further, in the present description, the holding frame includes the holding frame 10 in a state in which the imaging unit 30, for example, is not housed, and the holding frame 10 in a state in which the imaging unit 30 is housed in and connected to a housing portion 11.

The holding frame 10 is a cylindrical molded interconnect device (MID) molded by injection molding and formed with three-dimensional wiring, and is arranged at the distal end of the endoscope 2. In the first embodiment, the MID used as the holding frame 10 may be easily and inexpensively manufactured even in a complicated structure by forming the three-dimensional wiring at an arbitrary position. Examples of the material of the holding frame 10 include liquid crystal polymers, polyamides, and polycarbonates, for example. Using a molded interconnect device as the holding frame 10 allows the endoscope distal end structure 100 to be easily and inexpensively manufactured.

The holding frame 10 has a housing portion 11 of the imaging unit 30 which is formed by having the distal end face and the side face on the distal end side of the holding frame 10 notched, a channel insertion hole 12 through which a channel tube is inserted, and a light guide insertion hole 13 through which a light guide is inserted. The channel insertion hole 12 and the light guide insertion hole 13 are insertion holes penetrating from the distal end side to the proximal end side of the holding frame 10, and are arranged in parallel with the optical axis direction of the imaging unit 30.

The housing portion 11 is a recessed portion formed on the distal end side of the holding frame 10, in which a part of the distal end side face and a part of the side face of the holding frame 10 are opened. The housing portion 11 has a connection terminal 14 for electrically connecting the imaging unit 30 formed on its bottom face (a face perpendicular to the optical axis of the imaging unit 30). The connection lands, which are not illustrated in the figure, of the imaging unit 30 are electrically and mechanically connected to the connection terminals 14 by bumps including solder, for example. The connection terminal 14 includes a communication terminal including a clock required for driving the imaging unit 30, a power supply terminal, a ground terminal, and a signal output terminal, for example. Although not illustrated in FIG. 4, the gap between the imaging unit 30 and the housing portion 11 (including the connection portion between the imaging unit 30 and the connection terminal 14) and the side face portion of the imaging unit 30 not in contact with the housing portion 11 are covered with a resin such as an underfill.

The holding frame 10 has a first cut face f1 and a second cut face f2 formed on its cylindrical side face. The first cut face f1 and the second cut face f2 are faces obtained by cutting a support portion which is a gate portion into which a resin is injected when the holding frame 10 is resin-molded. The first cut face f1 and the second cut face f2 are arranged in parallel to face each other.

The holding frame 10 has, on its proximal end side, a cable connection electrode 16 arranged on a face where a part of its cylindrical outer periphery is notched. The signal cable 40 is such that an insulating jacket on the distal end side of the signal cable is removed to expose a core wire 41 and the exposed core wire 41 is connected to the cable connection electrode 16 by a conductive material such as solder, which is not illustrated in the figure.

The imaging unit 30 housed in the housing portion 11 has an optical unit, which is not illustrated in the figure, for forming an image of the subject, and an imaging element, which is not illustrated in the figure, for photoelectrically converting the subject image formed by the optical unit to generate an image signal, in which the imaging element includes a CCD or CMOS, for example.

The surface area of the holding frame 10 excluding the first cut face f1 and the second cut face f2 is formed with a wiring pattern 15 for electrically connecting the connection terminal 14 and the cable connection electrode 16. Forming the wiring pattern 15 on the surface area of the holding frame 10 excluding the first cut face f1 and the second cut face f2 allows a main body of a holding frame 10' to be molded by a plurality of molds arranged in an array, and three-dimensional wiring to be formed before being divided into individual pieces, so that the holding frame 10 may be easily manufactured.

Figure 5:
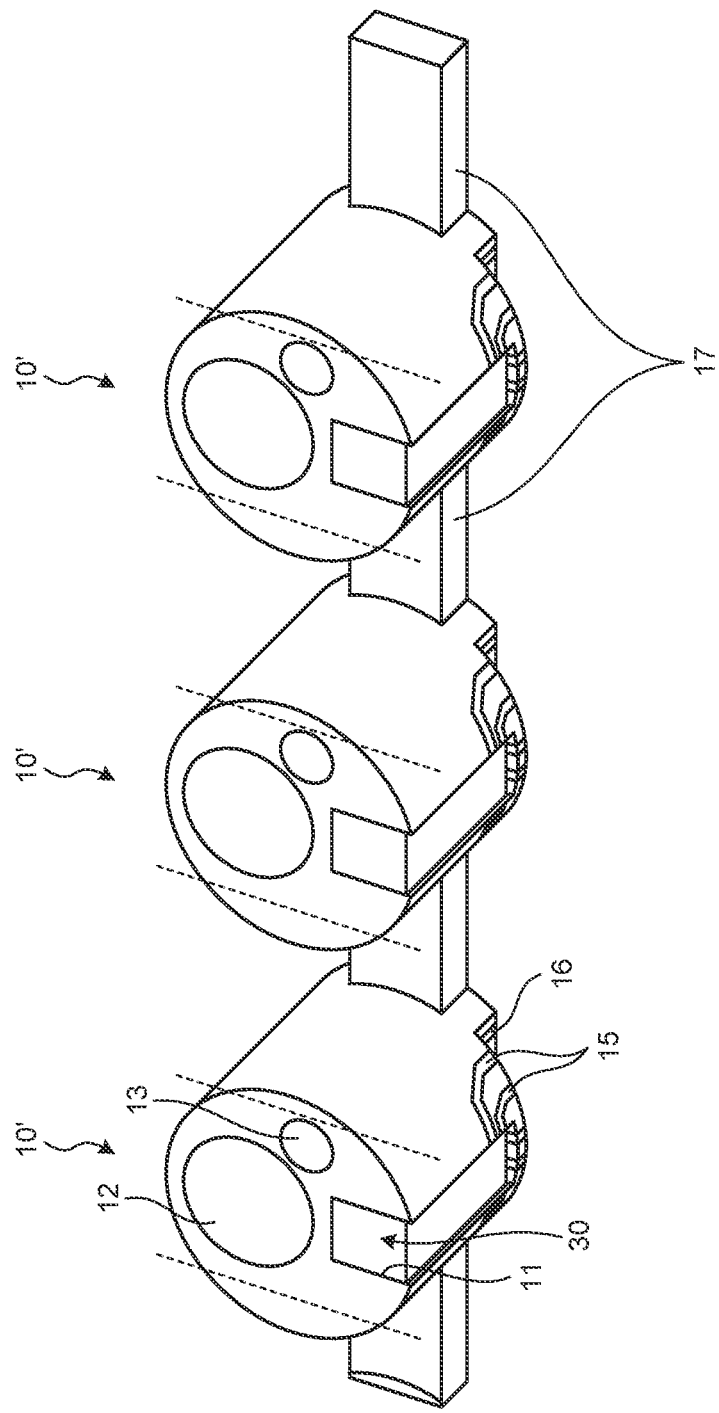
FIG. 5 is a view for explaining a manufacturing process of the holding frame of FIG. 2.

FIG. 5 is a view for explaining a manufacturing process of the holding frame 10. FIG. 5 illustrates the holding frame 10' arranged in an array before being divided into individual pieces. The holding frame 10' has the connection terminal 14, the wiring pattern 15 and the cable connection electrode 16 formed therein, and the housing portion 11 has the imaging unit 30 housed therein. The connection lands, which are not illustrated in the figure, of the imaging unit 30 are connected to the connection terminals 14 by bumps, for example. In FIG. 5, the holding frame 10' is connected by a support portion 17 which is a gate portion into which a resin is injected when the holding frame 10' is resin-molded.

The holding frame 10' connected by the support portion 17 is divided into individual pieces by cutting the support portion 17 and the side faces of the holding frame 10' at the cutting position indicated by the dotted line in FIG. 5 to form the holding frame 10. The cut faces of support portion 17 of the holding frame 10 and of the side faces of the holding frame are the first cut face f1 and the second cut face f2. In the first embodiment, since the wiring pattern 15 is formed in the surface area (side face of the holding frame 10 excluding the first cut face f1 and the second cut face f2 and the connection face of the signal cable 40) of the holding frame 10 excluding the first cut face f1 and the second cut face f2, the wiring pattern 15, the connection terminal 14 and the cable connection electrode 16 may be formed in the holding frame 10 before dividing the holding frames into individual pieces. The manufacturing process may avoid the complicated work of individually forming the wiring pattern 15 in the holding frame 10. In FIG. 5, although the imaging unit 30 is housed in the housing portion 11 of the holding frame 10' and connected thereto before the holding frames 10 are divided into individual pieces, the imaging unit 30 may be housed in the housing portion 11 and connected thereto after the holding frames 10 are divided into individual pieces without housing the imaging unit 30 in the housing portion 11 of the holding frame 10'.

When the support portion 17 is cut from the holding frame 10', the first cut face f1 and the second cut face f2 are cut so as to be positioned inside the circumscribed circle of the side face of the holding frame 10 (10'). FIG. 6 is a view for explaining the cut face of the holding frame 10, in which FIG. 6(a) illustrates a case where the first cut face f1 and the second cut face f2 are positioned outside the circumscribed circle of the side face of the holding frame 10 (10"), and FIG. 6(b) illustrates a case where the first cut face f1 and the second cut face f2 are positioned inside the circumscribed circle of the side face of the holding frame 10 (10').

As illustrated in FIG. 6(a), when the support portion 17 is cut at a cutting position P1, the first cut face f1 and the second cut face f2 are positioned outside the circumscribed circle of the side face of the holding frame 10 (10"), so that the circumscribed circle of the holding frame 10" is larger than the holding frame 10", as indicated by the dashed line in the figure, and thus the outer diameter of the endoscope 2 also becomes larger when the cut faces are used for the endoscope 2.

In the first embodiment, as illustrated in FIG. 6(b), the support portion 17 is cut at a cutting position P2, and the first cut face f1 and the second cut face f2 are positioned inside the circumscribed circle of the side face of the holding frame 10 (10'), so that the outer diameter of the endoscope 2 may be reduced when the cut faces are used for the endoscope 2.

Further, in the first embodiment, the first cut face f1 and the second cut face f2 are positioned inside the circumscribed circle of the side face of the holding frame 10, that is, the side face of the holding frame 10 is also cut when the support portion 17 is cut. Therefore, if the channel insertion hole 12 and the light guide insertion hole 13 provided in the holding frame 10 are arranged in the vicinity of the first cut face f1 and the second cut face f2, the thickness between the channel insertion hole 12 or the light guide insertion hole 13 and the outer peripheral face of the holding frame 10 may become thinner, and thus the strength of the holding frame may be reduced. Although the light guide insertion hole 13 is generally smaller in diameter than the channel insertion hole 12 and relatively easy to be adjusted for its arranged position, the channel insertion hole 12 is larger in diameter and required to be considered for its arranged position.

Figure 7A:
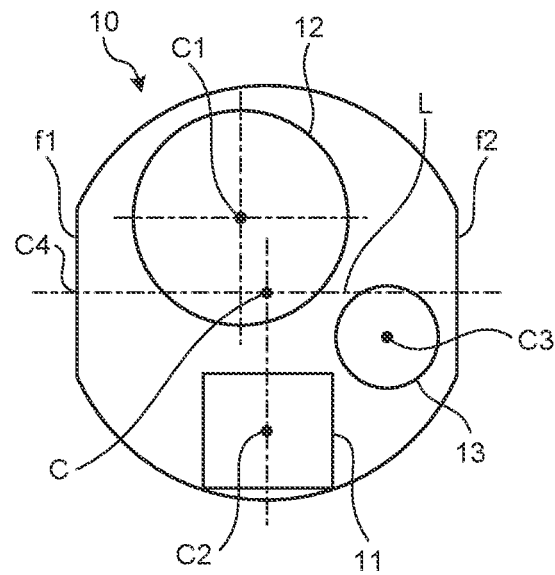
FIG. 7A is a view for explaining a position of a channel insertion hole of the holding frame of FIG. 2.
Figure 7B:
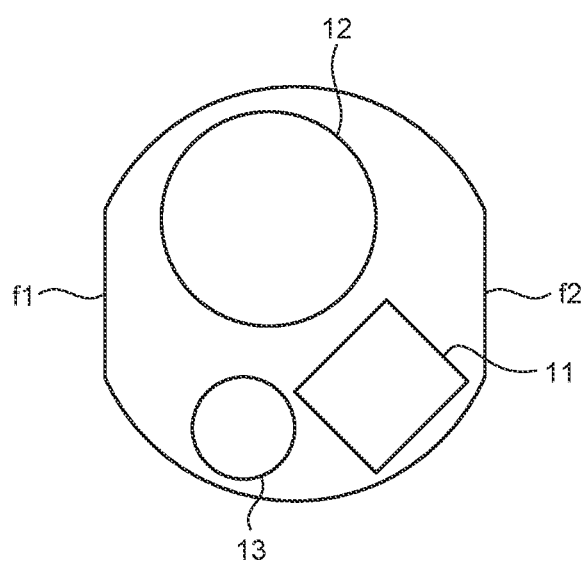
FIG. 7B is a view for explaining the position of the channel insertion hole of the holding frame of FIG. 2.

FIG. 7A is a view for explaining the position of the channel insertion hole 12 of the holding frame 10. In the first embodiment, the channel insertion hole 12 is arranged such that the center C1 of the channel insertion hole 12 is not positioned on a line L connecting the center C of the holding frame 10 and the center C4 of the first cut face f1 (or the second cut face f2). The arrangement may maintain the wall thickness around the channel insertion hole 12 and the strength of the holding frame 10. Further, the arrangement of the housing portion 11, the channel insertion hole 12, and the light guide insertion hole 13 in the holding frame 10 is not limited to that illustrated in FIG. 7A. The arrangement illustrated in FIG. 7B may be employed unless the center C1 of the channel insertion hole 12 is positioned on the line L connecting the center C of the holding frame 10 and the center C4 of the first cut face f1 (or the second cut face f2). For the endoscope having no channel, the center C2 of the housing portion 11 and the center C3 of the light guide insertion hole 13 are arranged so as not to be positioned on the line L connecting the center C of the holding frame 10 and the center C4 of the first cut face f1 (or the second cut face f2), thereby maintaining the wall thickness around the light guide insertion hole 13 and the strength of the holding frame.

The housing portion 11 is also not arranged so as to be positioned on the side of the first cut face f1 and the second cut face f2. Such a positioning of the housing portion is because the housing portion 11 has a structure in which a part of the side face of the holding frame 10 is opened and has enough thickness for the structure, but is not capable of forming the wiring pattern 15 before dividing into individual pieces by arranging the housing portion 11 on the cutting face side.

As described above, in the first embodiment, forming the wiring pattern 15 on the surface area of the holding frame 10 excluding the first cut face f1 and the second cut face f2 allows the holding frames 10 to be divided into individual pieces by cutting after forming the three-dimensional wiring and to be easily manufactured, even when the plurality of holding frames 10 are simultaneously formed by the plurality of molds arranged in an array.

Although the above-described first embodiment illustrates the holding frame 10 having two cut faces (the first cut face f1 and the second cut face f2), the first embodiment is not limited thereto. The holding frame may have one cut face or four cut faces. Although the first embodiment is such that the first cut face f1 and the second cut face f2 are arranged in parallel to face each other, the first embodiment is not limited to thereto. The arrangement may be such that the extension lines of the cut faces are orthogonal to each other.

Figure 8:
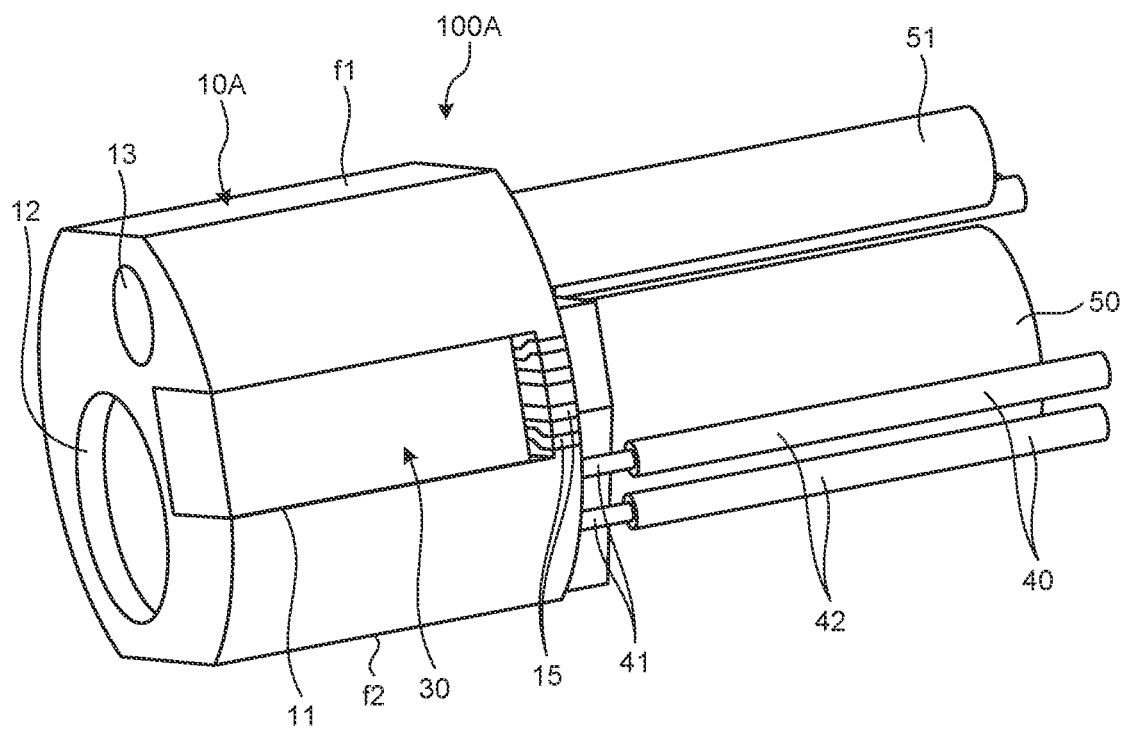
FIG. 8 is a perspective view of an endoscope distal end structure according to a second embodiment.
Figure 9:
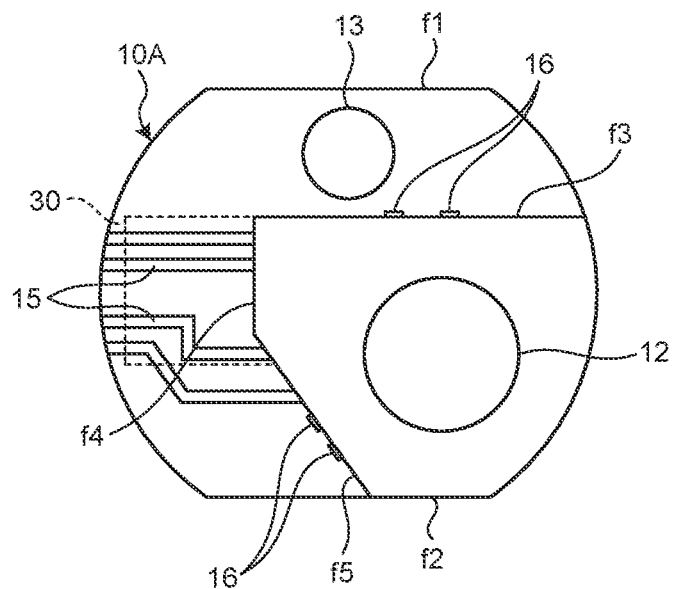
FIG. 9 is a perspective view of a proximal end side of the endoscope distal end structure of FIG. 8.
Figure 10:
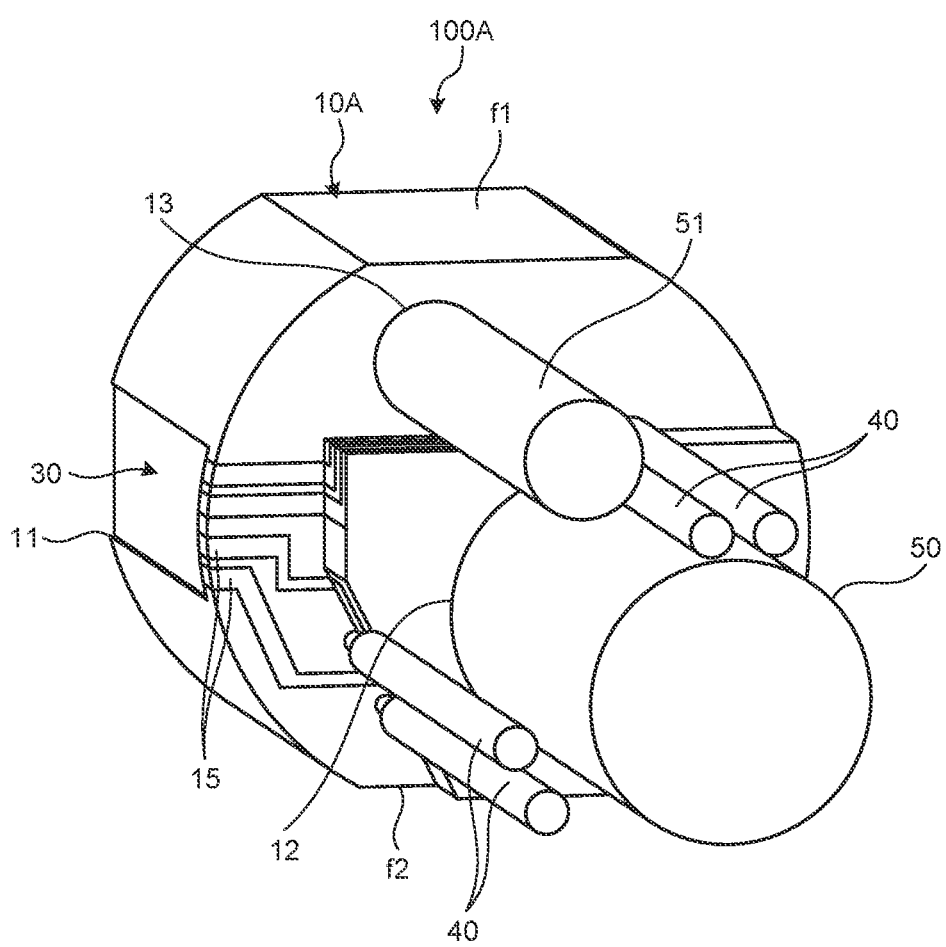
FIG. 10 is a view of a holding frame used in the endoscope distal end structure of FIG. 8 as viewed from its proximal end side.

The holding frame of the second embodiment is different from that of the first embodiment in that the cable connection electrode is arranged at a position not overlapping the projection area in the optical axis direction of the imaging unit. FIG. 8 is a perspective view of an endoscope distal end structure 100A according to the second embodiment. FIG. 9 is a perspective view of the proximal end side of the endoscope distal end structure 100A of FIG. 8. FIG. 10 is a view of a holding frame 10A used in the endoscope distal end structure 100A of FIG. 8 as viewed from its proximal end side.

In the present embodiment, the projection area of the imaging unit is an area (imaginary space that is hidden) that becomes a shadow when the imaging unit is viewed from the front direction (the direction of the distal end of the insertion unit 6). When light parallel to the optical axis is applied to the imaging unit from the front direction, the projection area has the same cross section as a shadow generated on a predetermined projection plane.

As illustrated in FIG. 9, the second embodiment provides a plurality of notched faces (f3, f4, f5) for arranging the cable connection electrodes 16. As illustrated in FIG. 10, the cable connection electrodes 16 formed on the notched faces f3 and f5 are arranged at positions that do not overlap the projection area in the optical axis direction of the imaging unit 30.

Figure 11:
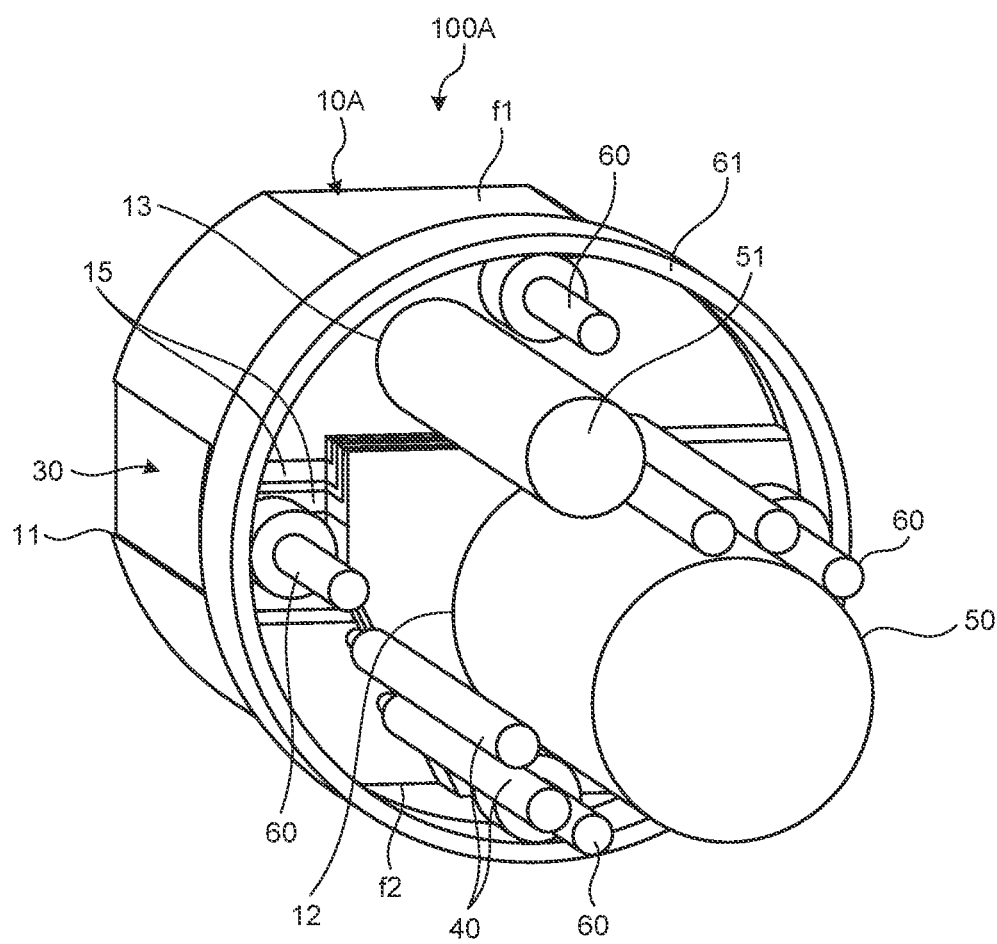
FIG. 11 is a view in which an angle wire is arranged in the endoscope distal end structure of FIG. 8.

FIG. 11 is a view in which an angle wire 60 is arranged in the endoscope distal end structure 100A of FIG. 8. FIG. 12 is a perspective view of the endoscope distal end structure 100A of FIG. 11 from another direction.

The angle wire 60 for performing bending operation of the bending portion 6b is fixed to the proximal end side of the endoscope distal end structure 100A through an angle wire fixing portion 61.

In the angle wire 60 for performing bending operation of the bending portion 6b, two angle wires 60 are used when bending in the vertical (or horizontal) direction, and four angle wires 60 are used to perform bending operation of the bending portion 6b when bending in the vertical and horizontal directions. When the operation is performed using two angle wires 60, the angle wires 60 are arranged vertically or horizontally. When four angle wires 60 are used, the angle wires 60 are arranged vertically and horizontally, respectively.

For the holding frame 10 of the first embodiment, when two angle wires 60 are used, the angle wires 60 and the signal cable 40 may be prevented from interfering with each other by arranging the angle wires on the first cut face f1 side and the second cut face f2 side, respectively. However, when four angle wires 60 are used, the angle wires 60 and the signal cable 40 interfere with each other.

For the holding frame 10A of the second embodiment, the angle wire 60 and the signal cable 40 may be prevented from interfering with each other by providing the plurality of notched faces (f3, f4, f5) for arranging the cable connection electrodes 16, arranging the cable connection electrodes 16 at positions that do not overlap the projection area in the optical axis direction of the imaging unit 30, and arranging one of the angle wires 60 at a position that overlaps the projection area in the optical axis direction of the imaging unit 30. The holding frame 10A according to the second embodiment is particularly effective when four angle wires 60 are used, but may be suitably used even when two angle wires 60 are used because the degree of freedom in the arrangement position of the cable connection electrodes 16 is increased.

The holding frame, the endoscope distal end structure, and the endoscope are useful for an endoscope system that requires a reduced diameter.

The present disclosure reduces the diameter of a distal end portion of an endoscope and manufacture endoscopes in a simple manner.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. A holding frame for use with an endoscope, the holding frame comprising:
    a main body comprising a cylindrical three-dimensional molded interconnect device, the main body comprising;
        a housing configured to house an image sensor, the housing being formed of a notch at a corner of a distal end face of the main body and a side face of a distal end side of the main body;
        at least one cut face extending entirely from a distal-most end to a proximal-most end of the side face of the main body;
        a connection terminal formed on a bottom face of the housing and configured to be connected to the image sensor;
        a cable connection electrode arranged on a face where a proximal end side of the main body is notched; and
        a wiring pattern formed on a surface area of the main body excluding the cut face and configured to electrically connect the connection terminal and the cable connection electrode.

2. The holding frame according to claim 1, wherein the cut face is positioned inside a circumscribed circle of a side face of the main body.

3. The holding frame according to claim 1, wherein the cut face includes a first cut face and a second cut face, and the first cut face and the second cut face are arranged in parallel to face each other.

4. The holding frame according to claim 1, comprising an insertion hole through which a channel or a light guide is inserted,
    wherein the insertion hole is arranged such that a center of the insertion hole is not positioned on a line connecting a center of the holding frame and a center of the cut face.

5. The holding frame according to claim 1, wherein the cable connection electrode is arranged at a face where a proximal end side of the main body is notched and does not overlap a projection area in an optical axis direction of the image sensor.

6. An endoscope distal end structure, comprising:
    an image sensor configured to capture a subject image;
    a signal cable configured to transmit and receive signals to and from image sensor;
    a holding frame for the image sensor, the holding frame having a main body comprising a cylindrical three-dimensional molded interconnect device;
    a plurality of angle wires; and
    a fixing portion configured to fix the angle wires,
    wherein the main body comprises:
        a housing configured to house the image sensor, the housing being formed of a notch at a corner of a distal end face of the main body and a side face of a distal end side of the main body;
        at least one cut face extending entirely from a distal-most end to a proximal-most end of the side face of the main body;
        a connection terminal formed on a bottom face of the housing and configured to be connected to the image sensor;

a cable connection electrode arranged on a face where a proximal end side of the main body is notched; and a wiring pattern formed on a surface area of the main body excluding the cut face and configured to electrically connect the connection terminal and the cable connection electrode, one of the plurality of angle wires is arranged at a position overlapping a projection area of the image sensor, and the cable connection electrode is arranged at a face where a proximal end side of the main body is notched and does not overlap a projection area in an optical axis direction of the image sensor.

7. The endoscope distal end structure according to claim 6, wherein the image sensor and the signal cable are positioned within a projection area in an optical axis direction of a distal end face of the main body.

8. The endoscope distal end structure according to claim 6, wherein the cut face is positioned inside a circumscribed circle of a side face of the main body.

9. The endoscope distal end structure according to claim 6, wherein the cut face includes a first cut face and a second cut face, and the first cut face and the second cut face are arranged in parallel to face each other.

10. The endoscope distal end structure according to claim 6, comprising an insertion hole through which a channel or a light guide is inserted, wherein the insertion hole is arranged such that a center of the insertion hole is not positioned on a line connecting a center of the holding frame and a center of the cut face.

11. The endoscope distal end structure according to claim 6, wherein the cable connection electrode is arranged at a face where a proximal end side of the main body is notched and does not overlap a projection area in an optical axis direction of the image sensor.

12. The endoscope distal end structure according to claim 6, wherein the cut face extends entirely from a distal-most end to a proximal-most end of the side face of the main body.

13. An endoscope comprising:

a holding frame arranged at a distal end of an insertion unit thereof, the holding frame comprising:

a main body comprising a cylindrical three-dimensional molded interconnect device, the main body comprising;

a housing configured to house an image sensor, the housing being formed of a notch at a corner of a distal end face of the main body and a side face of a distal end side of the main body;

at least one cut face formed extending entirely from a distal-most end to a proximal-most end of the side face of the main body;

a connection terminal formed on a bottom face of the housing portion and configured to be connected to the image sensor;

a cable connection electrode arranged on a face where a proximal end side of the main body; and a wiring pattern formed on a surface area of the main body excluding the cut face and configured to electrically connect the connection terminal and the cable connection electrode.

14. The endoscope according to claim 13, wherein the cut face is positioned inside a circumscribed circle of a side face of the main body.

15. The endoscope according to claim 13, wherein the cut face includes a first cut face and a second cut face, and the first cut face and the second cut face are arranged in parallel to face each other.

16. The endoscope according to claim 13, comprising an insertion hole through which a channel or a light guide is inserted, wherein the insertion hole is arranged such that a center of the insertion hole is not positioned on a line connecting a center of the holding frame and a center of the cut face.

17. The endoscope according to claim 13, wherein the cable connection electrode is arranged at a face where a proximal end side of the main body is notched and does not overlap a projection area in an optical axis direction of the image sensor.

* * * * *